United States Patent [19]

Prockop et al.

[11] Patent Number: 5,716,616
[45] Date of Patent: Feb. 10, 1998

[54] ISOLATED STROMAL CELLS FOR TREATING DISEASES, DISORDERS OR CONDITIONS CHARACTERIZED BY BONE DEFECTS

[75] Inventors: Darwin J. Prockop, Philadelphia; Ruth F. Pereira, Lansdowne; Dennis B. Leeper, Wynnewood; Michael D. O'Hara, Wyncote, all of Pa.

[73] Assignee: Thomas Jefferson University, Philadelphia, Pa.

[21] Appl. No.: 412,066

[22] Filed: Mar. 28, 1995

[51] Int. Cl.$^6$ ................................................. A61K 35/28
[52] U.S. Cl. ............... 424/93.7; 424/93.71; 424/93.72; 424/93.73
[58] Field of Search ............................. 424/93.7, 93.71, 424/93.72, 93.73

[56] References Cited

U.S. PATENT DOCUMENTS

| | | | |
|---|---|---|---|
| 4,608,199 | 8/1986 | Caplan et al. | 530/414 |
| 4,609,551 | 9/1986 | Caplan et al. | 424/95 |
| 4,620,327 | 11/1986 | Caplan et al. | 632/10 |
| 4,904,259 | 2/1990 | Itay | 623/16 |
| 5,197,985 | 3/1993 | Caplan et al. | 623/16 |
| 5,226,914 | 7/1993 | Caplan et al. | 623/16 |
| 5,486,359 | 1/1996 | Caplan et al. | 424/93.7 |

FOREIGN PATENT DOCUMENTS 0 381 490   8/1990   European Pat. Off. .

OTHER PUBLICATIONS

Nakagawa, et al., "Prevention of autoimmune inflammatory polyarthritis in male New Zealand black/KN mice by transplantation of bone marrow cells plus bone (stromal cells)." *Arthritis and Rheumatism*, 36(2), 1993, 263–268.

Anklesaria, P. et al., "Engraftment of a clonal bone marrow stromal cell line in vivo stimulates hematopoietic recovery from total body irradiation", *Proc. Natl. Acad. Sci. USA* 1987, 84, 7681–7685.

Appelbaum, F.R. et al., "Specific marrow ablation before marrow transplantation using and aminoposphonic acid conjugate $^{166}$Ho–EDTMP", *Blood* 1992, 80(6), 1608–1613.

Bennett, J.H. et al., "Adipocytic cells cultured from marrow have osteogenic potential", *Cell* 1991, 99, 131–139.

Beresford, J.N. et al., "Evidence for an adverse relationship between the differentiation of adipocytic and osteogenic cells in rat marrow stromal cell cultures", *J. of Cell Science* 1992, 102, 341–351.

Bienzle, D. et al., "Gene reansfer into hematopoietic cells; long–term maintenance of in vitro activated progenitors without morrow ablation", *Proc. Natl. Acad. Sci. USA* 1994, 91, 350–354.

Carter, R.F. et al., "Autologus transplantation of canine long–term marrow culture cells genetically marked by retroviral vectors", *Blood* 1992, 79(2), 356–364.

Castro–Malaspina, H. et al., "Characterization of human bone marrow fibroblast colony–forming cells (CFU–F) and their progeny", *Blood* 1980, 56(2), 289–301.

Coccia, P.F. et al., "Successful bone–marrow transplantation for infantile malignant osteopetrosis", *The New England Journal of Medicine* 1980, 302(13), 701–.

Friedenstein, A.J. et al., "Fibroblast precursors in normal and irradiated mouse hematopoietic organs", *Exp. Hemat.* 1976, 4, 267–274.

Khillan, J.S. et al., "Transgenic mice that express a mini––gene version of the human gene for type I procollagen (COL1A1) develop a phenotype resembling a lethal form of osteogenesis imperfecta", *J. of Biological Chemistry* 1991, 226(34), 23373–23379.

Kiefer, F. et al., "Fractionation of mouse bone marrow by adherence separates primitive hematopoietic stem cells from in vitro colony–forming cells and spleen colony–forming cells", *Blood* 1991, 78(10), 2577–2582.

Liesveld, J.L. et al., "Characterization of human marrow stromal cells: role in progenitor cell binding and granulopoiesis", *Blood* 1989, 73(7), 1794–1800.

Liesveld, J.L. et al., "Adhesive interactions of normal and leukemic human CD34$^+$ myeloid progenitors: role of marrow stromal, fibroblast, and cytomatrix components", *Exp. Hematol.* 1991, 19, 63–70.

Morrison, N.A. et al., "Prediction of bone density from vitamin D receptor alleles", *Nature* 1994, 367, 284–287.

Nakahara, H. et al., "Culture–expanded human periosteal–derived cells exhibit osteochondral potential in vivo", *J. of Orthopaedic Research* 1991, 9, 465–476.

Niedzwiedzki, T. et al., "Bone healing after bone marrow stromal cell transplantation to the bone defect", *Biomaterials* 1993, 14(2), 115–121.

O'Hara, M.D. et al., "The development of thermotolerance in bone marrow CFU–S during chronic hyperthermia", *Exp. Hematol.* 1991, 19, 878–881.

Ohgushi, H. et al., "Repair of bone defects with marrow cells porous ceramic", *Acta Orthop Scand* 1989, 60(3), 334–339.

(List continued on next page.)

*Primary Examiner*—Jean C. Witz
*Attorney, Agent, or Firm*—Woodcock Washburn Kurtz Mackiewicz & Norris LLP

[57] ABSTRACT

Methods of treating patients who are suffering from a disease, disorder or condition characterized by a bone cartilage or lung defect are disclosed. The methods comprising the step of intravenous administration of stromal cells isolated from normal syngeneic individuals or intravenous administration of stromal cells isolated from the patient subsequent to correction if the genetic defect in the isolated cells. Methods of introducing genes into a recipient individual are disclosed. The methods comprise the steps of obtaining a bone marrow sample from either the recipient individual or a matched syngeneic donor, isolating adherent cells from the sample, transfecting the adherent cells that were isolated from the recipient or a matched syngeneic donor with a gene and administering the transfected adherent cells to the recipient individual intravenously. Compositions that comprise isolated stromal cells that include exogenous genes operably linked to regulatory sequences are disclosed.

9 Claims, No Drawings

OTHER PUBLICATIONS

Piersma, A.H. et al., "Transplantation of bone marrow fibroblastoid stromal cells in mice via the intravenous route", *British Journal of Haematology* 1983, 54, 285–290.

Piersma, A.H. et al., "Characterization of fibroblastic stromal cells from murine bone marrow", *Exp. Hematol* 1985, 13, 237–243.

Simmons, P.J. and Torok–Storb, B., "Identification of stromal cell precursors in human bone marrow by a novel monoclonal antibody, STRO–1", *Blood* 1991, 78(1), 55–62.

Sokolov, B.P. et al., "Tissue–and development–specific expression in transgenic mice of a type I procollagen (COL1A1) minigene construct with 2.3 kb of the promoter region and 2 kb of the 3'–flanking region. Specificity is independent of the putative regulatory sequences in the first intron", *Biochemsistry* 1993, 32, 9242–9249.

Stewart, M. et al., "Long–term engraftment of normal and post –5–fluorouracil murine marrow into normal nonmyeloablated mice", *blood* 1993, 81(10), 2566–2571.

Wakitani, S. et al., "Mesenchymal cell–based repair of large, full–thickness defects of articular cartilage", *J. of Bone and Joint Surgery* 1994, 76–A(4), 579–592.

Pereira, R. et al., "Transgenic Mice Expressing a Partially Deleted Gene for Type I Procollagen (COL1A1)", *J. Clin. Invest.* 1993, 91, 709–716.

ISOLATED STROMAL CELLS FOR TREATING DISEASES, DISORDERS OR CONDITIONS CHARACTERIZED BY BONE DEFECTS

FIELD OF THE INVENTION

The present invention relates to compositions comprising isolated stromal cells including stromal cells transfected with heterologous DNA and to methods of treating individuals suffering from diseases associated with bone cartilage or lung tissue and/or methods of treating individuals suffering from diseases associated with genetic defects.

BACKGROUND OF THE INVENTION

Bone marrow transplants have been used for many decades in patients and they are now commonly used after extreme measures of chemotherapy and irradiation for cancer. Included in the bone marrow is a small fraction of cells which are often referred to as stem cells in that they are immature cells which throw off daughter cells that then mature into differentiated cells such as red cells and white cells.

Many recent efforts at gene therapy have pursued the strategy of isolating hematopoietic stem cells from bone marrow, genetically altering the cells ex vivo, and then returning the cells to patients. However, there are only about 1 cell per $10^5$ cells in bone marrow that can serve as repopulating stem cells. Therefore it is necessary to isolate cell fractions enriched for stem cells with procedures such as affinity chromatography with antibodies to cell surface antigens.

In addition to hematopoietic stem cells, marrow contains "stromal cells" which are mesenchymal precursor cells (Friedenstein, A. J. et al., *Exp. Hemat.* 4:267–274 (1976) which is incorporated herein by reference) that are characterized by their adherence properties when bone marrow cells are removed and put on to plastic dishes. Within about four hours, stromal cells adhere to the plastic and can thus be isolated by removing non-adhered cells form the dishes. These bone marrow cells that tightly adhere to plastic have been studied extensively (Castro-Malaspina, H. et al., *Blood* 56:289–301 (1980); Piersma, A. H. et al., *Exp. Hematol* 13:237–243 (1985); Simmons, P. J. and Torok-Storb, B., *Blood* 78:55–62 (1991); Beresford, J. N. et al., *J. Cell. Sci.* 102:341–351 (1992); Liesveld, J. L. et al., *Blood* 73:1794–1800 (1989); Liesveld, J. L. et al., *Exp. Hematot* 19:63–70 (1990); and Bennett, J. H. et al., *J. Call. Sci.* 99:131–139 (1991)) which are incorporated herein by reference.

Stromal cells are believed to participate in the creation of the microenvironment with the bone marrow in vivo. When isolated, stromal cells are initially quiescent but eventually begin dividing so that they can be cultured in vitro. Expanded numbers of stromal cells can be established and maintained. Stromal cells have been used to generate colonies of fibroblastic adipocytic and osteogenic cells when cultured under appropriate conditions. If the adherent cells are cultured in the presence of hydrocortisone or other selective conditions populations enriched for hematopoietic precursors or osteogenic cells are obtained (Carter, R. F. et al., *Blood* 79:356–364 (1992) and Bienzle, D. et al., *Proc. Natl. Acad. Sci USA*, 91:350–354 (1994)) which are incorporated herein by reference.

There are several examples of the use of stromal cells. Stromal cells have been used to produce fibrous tissue, bone or cartilage when implanted into selective tissues in vivo (Ohgushi, H. et al., *Acte. Orthop. Scand.* 60:334–339 (1989); Nakahara, H. et al. *J. Orthop. Res.* 9:465–476 (1991); Niedzwiedski, T. et al., *Biomaterials* 14:115–121 (1993); and Wakitani, S. et al., *J. Bone & Surg.* 76A:579–592 (1994)). In some reports, stromal cells were used to generate bone or cartilage in vivo when implanted subcutaneously with a porous ceramic (Ohgushi, H. et al. *Acta. Orthop. Scand.* 60:334–339 (1989)) intraperitoneally in a diffusion chamber (Nakahara, H. et al. *J. Orthop. Res.* 9:465–476 (1991)) percutaneously into a surgically induced bone defect (Niedzwiedski, T. et al. *Biomaterials.* 14:115–121 (1993)) or transplanted within a collagen gel to repair a surgical defect in a joint cartilage (Wakitani, S. et al. *J. Bone & Surg.* 76A:579–592(1994)). Piersma, A. H. et al. *Brit. J. Hematol.* 54:285–290 (1983) disclose that after intravenous bone marrow transplantation, the fibroblast colony-forming cells which make up the hemopoietic stroma lodge and remain in the host bone marrow. Stewart et al. (*Blood* 81:2566–2571 (1993)) recently observed that unusually large and repeated administrations of whole marrow cells produced long-term engraftment of hematopoietic precursors into mice that had not undergone marrow ablation. Also, Bienzle et al. (*Proc. Natl. Acad. Sci USA*, 91:350–354 (1994)) successfully used long-term bone marrow cultures as donor cells to permanently populate hematopoietic cells in dogs without marrow ablation. In some reports, stromal cells were used either as cells that established a microenvironment for the culture of hematopoietic precursors (Anklesaria, *PNAS USA* 84:7681–7685 (1987)) or as a source of an enriched population of hematopoietic stem cells (Kiefer, *Blood* 78(10):2577–2582 (1991)) .

There remains a need for a method for treating individuals suffering from diseases conditions and disorders associated with defects in bone, cartilage or lung cells.

There remains a need for a means to correct a genetic deficiency in an individual. There remains a need for methods of performing gene therapy so that individuals suffering from diseases conditions and disorders associated with defective genes can be provided with working copies of such genes.

There remains a need for a means to deliver the genetic material that encodes therapeutic proteins to individuals. There remains a need for methods of performing gene therapy so that individuals suffering from diseases conditions and disorders can be provided with genes whose expression will confer a therapeutic effect on the individual.

SUMMARY OF THE INVENTION

One aspect of the present invention relates to methods of treating patients who are suffering from a disease, disorder or condition characterized by a bone, cartilage or lung defect. The method comprises the steps of obtaining a bone marrow sample from a normal, matched, syngeneic donor, isolating adherent cells from the sample and, administering the isolated adherent cells to the patient by intravenous infusion.

Another aspect of the present invention relates to methods of treating patients who are suffering from a disease, disorder or condition that characterized by a mutated, non-functioning or under-expressed gene which results in a defect in the patient's bones, cartilage or lungs. The method comprises the steps of obtaining a bone marrow sample from the patient, isolating adherent cells from the sample, transfecting said adherent cells with a normal copy of said mutated, non-functioning or under-expressed gene that is operably linked to functional regulatory elements, and administering the transfected adherent cells to the patient by intravenously.

Another aspect of the invention relates to methods of introducing genes into a recipient individual. The methods comprise the steps of obtaining a bone marrow sample from either the recipient individual or a matched syngeneic donor, isolating adherent cells from the sample, transfecting the adherent cells with a gene and administering the transfected adherent cells to the recipient individual intravenously.

The present invention also relates to compositions that comprise isolated stromal cells that include exogenous genes operably linked to regulatory sequences.

DETAILED DESCRIPTION OF THE INVENTION

The present invention exploits the discovery that isolated, cultured stromal cells repopulate tissue, particularly bone, cartilage and lung tissue, when administered into the bloodstream of an individual. The stromal cells act as precursor cells which produce daughter cells that then mature into differentiated cells. Accordingly, stromal cells from a matched donor may be administered intravenously to individuals suffering from diseases involving bone, cartilage or lung cells in order to augment or replace the individual's bone, cartilage or lung cells. Stromal cells from a matched donor may be administered intravenously to individuals suffering from diseases associated with defective gene expression in bone, cartilage or lung cells in order to replace the individual's bone, cartilage or lung cells that don't express or under express a normal gene and/or express a mutated scene. Stromal cells may also be transfected with heterologous genes in gene therapy protocols. According to such aspects of the invention, matched donor stromal cells or stromal cells from an individual may be removed and genetically altered prior to reintroducing the cells into the individual. The cells may be genetically altered to introduce a gene whose expression has therapeutic effect on the individual. According to some aspects of the invention, stromal cells from an individual may be genetically altered to replace a defective gene and/or to introduce a gene whose expression has therapeutic effect on the individual.

The discovery that isolated stromal cells may be administered intravenously to repopulate tissue provides the means to systemically administer cells that have the potential to correct genetic defects and/or introduce the means to produce therapeutic proteins. Stromal cells may be isolated with relative ease and isolated stromal cells may be cultured to increase the number of cells available. Systemic administration provides greater distribution of therapeutic cells compared to local administration. Intravenous administration also affords ease, convenience and comfort at higher levels than other modes of administration. In many applications, systemic administration by intravenous infusion is more effective overall.

As used herein, the term "disease, disorder or condition characterized by a bone, cartilage or lung defect" is meant to refer to diseases, disorders and conditions which are caused by a genetic mutation in a gene that is expressed by bone cells, cells which make cartilage or lung cells such that one of the effects of such a mutation is manifested by abnormal structure and/or function of the bone, cartilage and lungs respectively.

In some aspects of the invention, individuals suffering from diseases and disorders that affect bone and that are characterized by a genetic defect may be treated by supplementing, augmenting and/or replacing defective or deficient bone cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects bone and that is characterized by a genetic defect is osteogenesis imperfecta. Another example of a disease or disorder that affects bone and that is characterized by a genetic defect is osteoporosis. Osteoporosis is frequently regarded as a multifactorial disease to which environmental factors such as diet and exercise contribute. However, studies of disease in twins, large families and large populations demonstrate that many individuals develop the disease primarily because of a genetic defect (see Morrison et al. *Nature* 367:284–287 (1994)). Individuals suffering from osteogenesis imperfecta may be administered stromal cells from a normal matched donor which replace the bone cells in the individual which have a mutated collagen gene. In such embodiments, the normal cells will compensate for the defective cells. In some embodiments, the normal cells may be prepared from the individual's own stromal cells, since cells with a mutated collagenous defect have a growth disadvantage compared to normal cells when grown in culture. Therefore, if stromal cells from an individual with osteogenesis imperfecta are grown as culture, they will gradually become enriched for normal cells. This embodiment will be particularly effective if the individual is a mosaic for the mutated collagen so that some of his or her cells contained the mutated collagen gene and others do not. In an alternative embodiment, stromal cells are isolated from an individual suffering from osteogenesis imperfecta and a normal gene for collagen I is inserted into the isolated stromal cells. The transfected cells are then reintroduced into the individual. A few individuals suffering from osteoporosis also have mutations in one of the two genes for collagen I and the same embodiments, will compensate for the defective cells. In most individuals with osteoporosis, the genes at fault are still unknown but are likely to be identified soon. In such individuals, normal cells will compensate for the defect. Also, when the genes at fault are identified and isolated, an alternative embodiment will be to isolate stromal cells from the individual, insert normal copy or copies of the mutated gene, and reintroduce the cells to the individual.

In some aspects of the invention, individuals suffering from diseases and disorders that affect cartilage and that are characterized by a genetic defect can be treated by supplementing, augmenting and/or replacing defective cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects cartilage and that is characterized by a genetic defect is chondrodysplasia which cause severe dwarfism, severe problems with joints and related problems. Individuals suffering from chondrodysplasia may be administered stromal cells from a normal matched donor which replace the cells that produce cartilage in the individual which have a mutated collagen gene. In such embodiments, the normal cells will compensate for the defective cells. In an alternative embodiment, stromal cells are isolated from an individual suffering from chondrodysplasia and a normal gene for collagen II is inserted into the isolated stromal cells. The transfected cells are then reintroduced into the individual. The embodiment with the collagen II gene will be useful for the 20% to 90% of individuals with various types of severe chondrodysplasia. The remaining individuals with chondrodysplasia have mutations in other collagen genes (collagen X and X1), in other genes (fibroblast growth factor receptor 3), and in still unidentified genes. In such individuals, normal cells will compensate for the defective cells. Also, an alternative embodiment will be to isolate stromal cells from the individual, insert a normal copy or copies of the mutated gene, and reintroduce the cells to the individual. Another example of a disease or disorder that affects cartilage is osteoarthritis. Osteoarthritis is a heterogeneous disease both in terms of etiology and manifestations. Some individuals develop the degeneration of cartilage in joints that characterize osteoarthritis because of trauma or the late sequelae of infections. A few individuals develop osteoarthritis in multiple joints because of mutations in the gene for collagen II similar to the mutations in the gene that cause chondrodysplasia. Such individuals may or may not show signs of a mild chondrodysplasia. The cause of osteoarthritis in other individuals is unknown, but studies in large families suggest that the disease is inherited and therefore caused mutations is still unidentified genes. Therefore the same embodiments that will be useful to compensate for mutated genes in individuals with chondrodysplasia will also be useful for many individuals with osteoarthritis.

In some aspects of the invention, individuals suffering from diseases and disorders that affect the lungs and that are characterized by a genetic defect can be treated by supplementing, augmenting and/or replacing defective cells with cells that correctly express a normal gene. The cells may be derived from stromal cells of a normal matched donor or stromal cells from the individual to be treated. If derived from the individual to be treated, the cells may be genetically modified to correct the defect. An example of a disease or disorder that affects the lungs and that is characterized by a genetic defect is cystic fibrosis. Another example of a disease or disorder that affects the lungs and that is characterized by a genetic defect is a deficiency of $\alpha$1-antitrypsin. Individuals suffering from cystic fibrosis may be administered stromal cells from a normal matched donor which have a norma cystic fibrosis to replace or supplement the lungs cells in the individual which have a mutated cystic fibrosis gene. In such embodiments, the normal cells will compensate for the defective cells. In an alternative embodiment, stromal cells are isolated from an individual suffering from cystic fibrosis and a normal cystic fibrosis gene is inserted into the isolated stromal cells. The transfected cells are then reintroduced into the individual.

In addition to replacing cells that are defective with repaired cells or normal cells from matched donors, the invention may also be used to express desired proteins that are secreted. That is, stromal cells may be isolated, furnished with a gene for a desired protein and introduced into an individual within whom the desired protein would be produced and exert or otherwise yield a therapeutic effect. This aspect of the invention relates to gene therapy in which therapeutic proteins are administered to an individual. According to these aspects of the invention, the isolated stromal cells are vectors for introducing therapeutic genes into the individual as well as hosts for such genes when the cells are administered to the individual. The isolated stromal cells may be from matched donors or the individuals to be treated with the transfected stromal cells. In some embodiments, stromal cells are transfected with genes for which the individual to be treated suffers from a complete absence of a non-mutated copy of the gene, or suffers from an absence or insufficient expression of a non-mutated form of the protein. Stromal cells are transfected with a non-mutated copy of the gene in an expressible form. That is, the protein encoded by the transfected gene will be expressed by the stromal cells, preferably as a secreted protein. Examples of diseases, conditions or disorders in which defective genes or insufficient gene expression is causally linked to the disease or symptoms include, but are not limited to, growth hormone deficiency, diabetes, adenine deaminase deficiency, hemophilia A and hemophilia B. Other genetic diseases which may be treated using methods of the invention include: $\alpha_1$-antitrypsin deficiency, Fabray disease, familial hypercholesterolemia, Gaucher's disease, Lesch-Nyhan Syndrome, Maple syrup urine disease, Ornithine transcarbamylase deficiency, phenylketonuria, Sandhoff disease, Tay-Sachs disease and von Willebrand disease. By introducing normal genes in expressible form which encode, growth hormone, insulin, adenine deaminase or an appropriate blood clotting factor, individuals suffering from growth hormone deficiency, diabetes, adenine deaminase deficiency, and hemophilia, respectively, can be provided the means to compensate for genetic defects and eliminate, alleviate or reduce some or all of the symptoms associated with such diseases.

Similarly, in some embodiments, stromal cells are transfected with genes that encode proteins which will have a therapeutic effect when expressed in the individual to be treated. Rather than administering the therapeutic protein directly and at a series of time intervals, the present invention provides a means of administering a therapeutic protein continuously by administering cells which produce the protein. Stromal cells are transfected with a gene that encodes the protein in an expressible form. That is, the protein encoded by the transfected gene will be expressed by the stromal cells, preferably as a secreted protein. Examples of therapeutic proteins include, but are not limited to, granulocyte-macrophage colony stimulating factor, granulocyte colony stimulating factor, erythropoietin, interleukin-2 and interleukin-1 receptor antagonist protein.

In all cases in which a gene is transfected into a stromal cell, the gene is operably linked to regulatory sequences required to achieve expression of the gene in the stromal cell or the cells that arise from the stromal cells after they are infused into an individual. Such regulatory sequences include a promoter and a polyadenylation signal.

As used herein, the terms "exogenous genetic material" and "exogenous gene" are used interchangeably and meant to refer to genomic DNA, cDNA, synthetic DNA and RNA, mRNA and antisense DNA and RNA which is introduced into the stromal cell. The exogenous genetic material may be heterologous or an additional copy or copies of genetic material normally found in the individual or animal. When cells are used as a component of a pharmaceutical composition in a method for treating human diseases, conditions or disorders, the exogenous genetic material that is used to transform the cells may encode proteins selected as therapeutics used to treat the individual and/or to make the cells more amenable to transplantation.

The exogenous genetic material is preferably provided in an expression vector which includes the coding sequence for a protein whose production by the cells is desirous operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof or an RNA molecule such as mRNA.

The exogenous genetic material that includes the nucleotide sequence encoding the protein operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements necessary for gene expression include: a promoter, an initiation codon, a stop codon, and a polyadenylation signal. It is necessary that these elements be operable in the stromal cells or in cells that arise from the stromal cells after infusion into an individual. Moreover, it is necessary that these elements be operably linked to the nucleotide sequence that encodes the protein such that the nucleotide sequence can be expressed in the stromal cells and thus the protein can be produced. Initiation codons and stop codon are generally considered to be part of a nucleotide sequence that encodes the protein. However, it is necessary that these elements are functional in the stromal cells or cells that arise from stromal cells. Similarly, promoters and polyadenylation signals used must be functional within the stromal cells or cells that arise from stromal cells. Examples of promoters useful to practice the present invention include but are not limited to promoters that are active in many cells such as the cytomegalic virus promoter, SV40 promoters and retroviral promoters.

Other examples of promoters useful to practice the present invention include but are not limited to tissue-specific promoters, i.e. promoters that function in some tissues but not in others.

According to some embodiments, desired genes for transfection into stromal cells are operably linked to the human procollagen I promoter, human procollagen II promoter, and the human procollagen III promoter. In some embodiments, the genes are linked to relatively short 5'-fragments from either the COL1A1 or COL2A1 gene which comprise the promoter together with the some of the 5' translated and/or untranslated sequences of the gene. In some embodiments, the gene to be transfected is operably linked to a sequence that contains a 1.9 kb SphI-HindIII fragment from the 5'-end of the human COL1A1. The fragment contains from −476 bp to +1440 bp of COL1A1 gene and, therefore, includes the promoter (476 bp), exon 1 (222 bp) and most of the intron 1 (1223 bp of a total of 1453 bp). In some embodiments, the gene to be transfected is operably linked to a sequence that contains a fragment from the 5'-end of the human COL2A1. In some embodiments, the fragment contains −4.0 kb of the COL2A1 promoter and the complete COL2A1 gene the one or more exons and introns sequentially from exon 1 to exon 15 and intron 1 to intron 14. Some constructs may be designed as taught in co-pending U.S. Ser. No. 08/184,260 filed Jan. 18, 1994 entitled "Methods of targeting DNA insertion into genome", which is incorporated herein by reference.

Examples of polyadenylation signals useful to practice the present invention includes but is not limited to human collagen I polyadenylation signal, human collagen II polyadenylation signal, and SV40 polyadenylation signal.

In order for exogenous genetic material in an expression vector to be expressed, the regulatory elements must be operably linked to the nucleotide sequence that encodes the protein. In order to maximize protein production, regulatory sequences may be selected which are well suited for gene expression in the desired cells. Moreover, codons may be selected which are most efficiently transcribed in the cell. One having ordinary skill in the art can produce exogenous genetic material as expression vectors which are functional in the desired cells.

It is also contemplated that regulatory elements may be selected to provide tissue specific expression of the protein. Thus, for example, lung specific promoters may be provided such that if the administered stromal cells repopulate the lungs and the bone, the heterologous protein encoded by the gene construct in the transfected stromal cell will only be expressed in the cells that populate the lung.

In addition to providing cells with genetic material that either 1) corrects genetic defects in the cells, 2) encodes proteins which are otherwise not present in sufficient quantities and/or functional condition so that the genetic material corrects genetic defects of the individual, and/or 3) encodes proteins which are useful as therapeutics in the treatment of a particular disease or disorder, genetic material may also be introduced into the stromal cells used in the present invention to provide a means for selectively terminating such cells should such termination become desirable. Such means for targeting cells for destruction may be introduced into stromal cells which are to be otherwise genetically modified as well as those to which no other exogenous genetic material is to be introduced.

According to the invention, isolated stromal cells are furnished with genetic material which renders them specifically susceptible to destruction. For example, the stromal cells may be provided with genes that encode a receptor that can be specifically targeted with a cytotoxic agent. An expressible form of a gene that can be used to induce selective cell death can introduced into the cells. In such a system, cells expressing the protein encoded by the gene are susceptible to targetted killing under specific conditions or in the presence or absence of specific agents. For example, an expressible form of a herpes virus thymidine kinase (herpes tk) gene can be introduced into the cells and used to induce selective cell death. When the exogenous genetic material that includes (herpes tk) gene is introduced into the individual, herpes tk will be produced. If it is desirable or necessary to kill the transplanted cells, the drug gangcyclovir can be administered to the individual and that drug will cause the selective killing of any cell producing herpes tk. Thus, a system can be provided which allows for the selective destruction of transplanted cells.

As stated above, stromal cells may be derived from the individual to whom they will be administered (self donor) or from a matched donor. Those having ordinary skill in the art can readily identify matched donors using standard techniques and criteria. As used herein, the term donor is meant to refer to self donors and matched donors.

Those having ordinary skill in the art can identify individuals suffering from genetic diseases such as osteogenesis imperfecta, chondrodysplasia, cystic fibrosis, growth hormone deficiency, diabetes, adenine deaminase deficiency, hemophilia, osteoporosis, and osteoarthritis routinely using standard diagnostic procedures.

Stromal cells may be obtained by removing bone marrow cells from a donor and placing the cells in a sterile container with a plastic surface or other appropriate surface that the cells come into contact with. The stromal cells will adhere to the plastic surface within 30 minutes to about 6 hours. After at least 30 minutes, preferably about four hours, the non-adhered cells may be removed and discarded. The adhered cells are stromal cells which are initially non-dividing. After about 2–4 days however the cells begin to proliferate and can be cultured to increase their numbers using standard cell culture techniques.

Depending upon cell culture conditions, stromal cells will become hematopoietic or osteogenic precursors. Stromal cells have been used to generate colonies of fibroblastic, adipocytic and osteogenic cells when cultured under appropriate conditions. For example, the adherent cells are cultured in the presence of hydrocortisone or other selective conditions, populations enriched for hematopoietic precursors or osteogenic cells are obtained.

According to preferred embodiments, stromal cells are cultured in medium supplemented with 2–20% fetal calf serum or serum-free medium with or without additional supplements.

If foreign genes are to be introduced into stromal cells, standard methods are employed for introducing gene constructs into cell which will express the proteins encoded by the genes. In some embodiments, cells are transfected by calcium phosphate precipitation transfection, DEAE dextran transfection, electroporation or microinjection. A second gene is usually co-transfected or linked to the therapeutic gene. The second gene is frequently a selectable antibiotic-resistance gene. Transfected cells can be selected by growing the cells in an antibiotic that will kill cells that do not take up the selectable gene. In most cases where the two genes are unlinked and co-transfected, the cells that survive the antibiotic treatment have both genes in them and express both of them.

After isolating the stromal cells, the cells can be administered upon isolation or after they have been cultured. Isolated stromal cells administered upon isolation are administered within about one hour after isolation. Generally, stromal cells may be administration immediately upon isolation in situations in which the donor is large and the recipient is an infant. It is preferred that stromal cells are cultured prior to administrations. Isolated stromal cells can be cultured from 1 hour to over a year. In some preferred embodiments, the isolated stromal are cultured prior to administration for a period of time sufficient to allow them to convert from non-cycling to replicating cells. In some embodiments, the isolated stromal cells are cultured for 3–30 days, preferably 5–14 days, more preferably 7–10 days. In some embodiments, the isolated stromal cells are cultured for 4 weeks to a year, preferably 6 weeks to 10 months, more preferably 3–6 months.

If the cells are transfected, either 1) isolated, non-cycling stromal cells are first transfected and then administered as non-cycling cells, 2) isolated, non-cycling stromal cells are first transfected, then cultured for a period of time sufficient to convert from non-cycling to replicating cells and then administered, 3) isolated, non-cycling stromal cells are first cultured for a period of time sufficient to convert from non-cycling to replicating cells, then transfected, and then administered, or 4) isolated, non-cycling stromal cells are first cultured for a period of time sufficient to convert from non-cycling to replicating cells, then transfected, then cultured for Y days and then administered. In some embodiments, stromal cells are isolated, transfected and immediately administered. It is preferred that stromal cells are cultured prior to transfection and/or administrations. Isolated stromal cells can be cultured from cultured for 3–30 days, in some embodiments 5–14 days, in some embodiments 7–10 days prior to transfection. Transfected stromal cells can be cultured from cultured for 3–30 days, in some embodiments 5–14 days, in some embodiments 7–10 days prior to administration. Isolated stromal cells can be cultured from cultured for 3–30 days, in some embodiments 5–14 days, in some embodiments 7–10 days prior to transfection and upon transfection, additionally cultured for 3–30 days, in some embodiments 5–14 days, in some embodiments 7–10 days prior to administration. In some embodiments, the isolated stromal cells are cultured for 4 weeks to a year, in some embodiments 6 weeks to 10 months, in some embodiments 3–6 months prior to transfection. Transfected stromal cells can be cultured for 4 weeks to a year, in some embodiments 6 weeks to 10 months, in some embodiments 3–6 months prior to administration. In some embodiments, the isolated stromal cells are cultured for 4 weeks to a year, in some embodiments 6 weeks to 10 months, in some embodiments 3–6 months prior to transfection and upon transfection, further cultured for 4 weeks to a year, in some embodiments 6 weeks to 10 months, in some embodiments 3–6 months prior to administration.

Isolated stromal cells may be transfected using well known techniques readily available to those having ordinary skill in the art. In some embodiments, recombinant adenovirus vectors are used to introduce DNA with desired sequences into the stromal cell. In some embodiments, standard $CaPO_4$, DEAE dextran or lipid carrier mediated transfection techniques are employed to incorporate desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into isolated stromal cells.

For administration of stromal cells, the isolated stromal cells are removed from culture dishes, washed with saline, centrifuged to a pellet and resuspended in a glucose solution which is infused into the patient. In some embodiments, bone marrow ablation is undertaken prior to infusion in order to make space in the bone for introduced cells. Bone marrow ablation may be accomplished by X-radiating the individual to be treated, administering drugs such as cyclophosphamide or by a combination of X-radiation and drug administration. In some embodiments, bone marrow ablation is produced by administration of radioisotopes known to kill metastatic bone cells such as, for example, radioactive strontium, $^{135}$Samarium or $^{166}$Holmium (see Applebaum, F. R. et al. 1992 *Blood* 80(6):1608–1613, which is incorporated herein by reference).

If bone marrow ablation precedes administration of stromal cells, the administration of stromal cells must be accompanied by the administration of non-adherent cells which comprise blood cell precursors necessary for survival. Such non-adherent cells may be saved from the same sample used as starting materials in the isolation of stromal cells and stored or they can be derived from a different sample. In some preferred embodiments, the non-adherent cells are provided by the recipient/patient. Prior to procedures which generate bone marrow ablation, a sample of the patient/recipients bone marrow is obtained and stored. The entire sample may be used or the non-adherent cells may be isolated and used to administer in conjunction with isolated stromal cells. Non-adherent cells administered in conjunction with administration of stromal cells may be administered separately before or after stromal cell administration or may be mixed with isolated stromal cells prior to administration.

Bone marrow ablation is optional. In some embodiments, partial but not complete bone marrow ablation is produced prior to administration of stromal cells. In some embodiments, stromal cells are administered without any bone marrow ablation.

Between $10^7$ and $10^{13}$ cells per 100 kg person are administered per infusion. In some embodiments, between about $1-5 \times 10^8$ and $1-5 \times 10^{12}$ cells are infused intravenously per 100 kg person. In some embodiments, between about $1 \times 10^9$ and $5 \times 10^{11}$ cells are infused intravenously per 100 kg person. In some embodiments, $4 \times 10^9$ cells are infused per 100 kg person. In some embodiments, $2 \times 10^{11}$ cells are infused per 100 kg person.

In some embodiments, a single administration of cells is provided. In some embodiments, multiple administrations are provided. In some embodiments, multiple administrations are provided over the course of 3–7 consecutive days. In some embodiments, 3–7 administrations are provided over the course of 3–7 consecutive days. In some embodiments, 5 administrations are provided over the course of 5 consecutive days.

In some embodiments, a single administration of between $10^7$ and $10^{13}$ cells per 100 kg person is provided. In some embodiments, a single administration of between about $1-5 \times 10^8$ and $1-5 \times 10^{12}$ cells per 100 kg person is provided. In some embodiments, a single administration of between about $1 \times 10^9$ and $5 \times 10^{11}$ cells per 100 kg person is provided. In some embodiments, a single administration of $4 \times 10^9$ cells per 100 kg person is provided. In some embodiments, a single administration of $2 \times 10^{11}$ cells per 100 kg person is provided.

In some embodiments, multiple administrations of between $10^7$ and $10^{13}$ cells per 100 kg person are provided. In some embodiments, multiple administrations of between about $1-5 \times 10^8$ and $1-5 \times 10^{12}$ cells per 100 kg person are provided. In some embodiments, multiple administrations of between about $1 \times 10^9$ and $5 \times 10^{11}$ cells per 100 kg person are provided over the course of 3–7 consecutive days. In some embodiments, multiple administrations of $4 \times 10^9$ cells per 100 kg person are provided over the course of 3–7 consecutive days. In some embodiments, multiple administrations of $2 \times 10^{11}$ cells per 100 kg person are provided over the course of 3–7 consecutive days. In some embodiments, 5 administrations of $3-5 \times 10^9$ cells are provided over the course of 5 consecutive days. In some embodiments, 5 administrations of $4 \times 10^9$ cells are provided over the course of 5 consecutive days. In some embodiments, 5 administrations of $1-3 \times 10^{11}$ cells are provided over the course of 5 consecutive days. In some embodiments, 5 administrations of $2 \times 10^{11}$ cells are provided over the course of 5 consecutive days.

EXAMPLE

Cells from a transgenic mouse line that expresses a human mini-gene for collagen I in a tissue-specific manner were used to see whether precursor mesenchymal cells from marrow that are expanded in culture can serve as long-term precursors of bone and other connective tissues after intravenous infusion into irradiated mice. The marker gene consisted of an internally deleted mini-gene for the human proα1(I) chain of procollagen I that caused synthesis of shortened proα1(I) chains (Khillan, J. S. et al., *J. Biol. Chem.* 266:23373–23379 (1991); Pereira, R. et al., *J. Clin. Invest.* 91:709–716 (1983); and Sokolov, B. P. et al., *Biochemistry* 32:9242–9249 (1993)) which are incorporated herein by reference. Cells expressing the gene were obtained from a line of transgenic mice in which the copy number of the human mini-gene relative to the endogenous mouse gene was about 100 to 1, and the steady-state levels of mRNA from the human mini-gene relative to mRNA from the endogenous mouse gene was about 0.5:1 in most tissues.

Donor cells from marrow partially enriched for mesenchymal precursors were prepared by standard protocols (Friedenstein, A. J. et al., *Exp. Hemat.* 4:267–274 (1976); Castro-Malaspina, H. et al., *Blood* 56:289–301 (1980); Piersma, A. H. et al., *Exp. Hematol* 13:237–243 (1985; Simmons, P. J. and Torok-Storb, B., *Blood* 78:55–62 (1991); Beresford, J. N. et al., *J. Cell. Sci.* 102:341–351 (1992); Liesveld, J. L. et al., *Blood* 73:1794–1800 (1989); Liesveld, J. L. et al., *Exp. Hematot* 19:63–70 (1990); and Bennett, J. H. et al., *J. Call. Sci.* 99:131–139 (1991)) which are incorporated herein by reference. Briefly, the ends of long bones from the transgenic mice were cut, and the marrow was extracted with a pressurized syringe filled with α-MEM (Sigma) containing 10% fetal bovine serum (Atlanta Biologicals). About $10^7$ nucleated cells were plated onto 175 $cm^2$ plastic culture flasks in 25 ml of α-MEM containing 10% fetal bovine serum. After 4 h, the non-adherent cells were discarded by replacing the medium. Foci containing two to four fibroblast-like cells appeared in 2 to 3 days, and the foci grew to near-confluent colonies in about 1 wk. The yield was about $10^7$ cells per flask after trypsin digestion. By phase-contrast microscopy, most of the cells were fibroblast-like, but a few macrophages and adipocytes were also seen.

About $10^5$ of the cultured adherent cells were mixed with $6 \times 10^5$ non-adherent cells obtained by incubation of marrow from normal mice for 4 h on 175 $cm^2$ flasks under the same conditions used for the initial isolation of the adherent cells. The mixture of about $7 \times 10^5$ cells in 0.2 to 0.4 ml of α-MEM and 10% fetal bovine serum was injected into the tail vein of each recipient mouse.

Eight-week old mice from the same inbred FVB/N line were prepared to receive the donor cells by irradiation with a $^{137}$Cu irradiator (Atomic Energy of Canada, Ltd.). The unit had a dose rate of 116 cG/min with a parallel opposed beam configuration. Each animal received 9.0 Gy in two fractions with a 4 h interval (4.5 Gy+4.5 Gy) (O'Hara, M. D. et al., *Exp. Hemat* 19:878–881 (1991)). One to 2 h after the second radiation fraction, the mixture of marked adherent cells and normal non-adherent cells was injected intravenously. Control irradiated mice that did not receive a cell infusion died after 10 to 13 days of marrow failure.

To follow the fate of the donor cells, two PCR assays for the human COL1A1 mini-gene and the mouse endogenous COL1A1 gene were developed. With a two-primer assay, the values for the ratio of the human to mouse gene were linear over a range of $10^{-4}$ to about $10^{+1}$ and, therefore, of about $10^{-6}$ to $10^{-1}$ donor cells per recipient cell. With the three-primer assay, the values were linear over a range of about $10^{-3}$ to $10^{+2}$ and, therefore, about $10^{-5}$ to 1 donor cell per recipient cell.

Assays of irradiated mice after one day indicated only trace amounts of the donor cells in marrow, spleen, bone, lung or brain (Table 1). Slightly higher levels were seen at seven days. At 30 days and 150 days, progeny of the donor cells accounted for 2.0 to 12% of the cells in marrow, spleen, bone and lung (Table 1). At 150 days, they also accounted for 1.5 to 5.0% of the cells in xiphoid cartilage that was dissected free of any mineralized or fibrous tissue under a microscope. Although the mean values appeared to show a decrease between 1 and 5 months, there was no statistically significant decrease in the combined values for marrow, spleen, bone and lung between these two time periods (Table 1). Assays of non-irradiated mice revealed only very low levels of the donor cells at the same time points (<0.0001 to 0.05%). PCR in situ assay of tissue sections of lung demonstrated that progeny of the donor cells were evenly distributed in the parenchyma of both alveoli and bronchi.

To confirm that progeny of the donor cells were present in cartilage, chondrocytes were isolated from xiphoid and articular cartilage by digestion at 37° C. overnight with 0.5 mg/ml bacterial collagenase (Sigma) in DMEM. PCR assays indicated that progeny of the donor cells accounted for 2.5% of the isolated chondrocytes.

To determine whether the donor cells became functional mesenchymal cells in the tissues they populated, tissues from the recipient mice were assayed by RT-PCR for expression of the human mini-gene for collagen I contained in the donor cells. In three mice assayed at 150 days, the mini-gene was expressed in bone, a tissue in which over half the protein synthesized is collagen I. The expression in bone was confirmed by a similar assay on bone cells isolated from femur and cultured for 1 wk. Expression of the mini-gene for collagen I was more variable in marrow, spleen and lung, tissues in which the rate of collagen I synthesis is less than in bone. As expected, the mini-gene was not expressed in cartilage, a tissue in which about half the protein synthesized is collagen II but in which there is no synthesis of collagen I. The mini-gene for collagen I was also not expressed in cultures of chondrocytes from the recipient mice that contained the marker gene and that synthesize collagen II but not collagen I.

Earlier reports have shown that assays of the cells with cytochemical markers or for mRNAs indicated that the cells synthesized collagen I, collagen III, fibronectin, alkaline phosphatase and osteopontin, but did not have features characteristic of macrophages, granulocytes, T lymphocytes, B lymphocytes or endothelial cells. The results here demonstrate that after intravenous injection into irradiated mice, the expanded cultures of adherent cells efficiently populate several connective tissues. The results also demonstrate that the cells serve as true precursor cells for these tissues, since they expressed the marker gene for collagen I in a tissue-specific manner, and they were diffusely incorporated into the mesenchymal parenchyma of lung.

TABLE 1

RE-POPULATION OF TISSUE BY ADHERENT MARROW CELLS INTRAVENOUSLY ADMINISTERED TO IRRADIATED MICE

| | Donor cells (% of total)* | | | | | | | | | | | |
|---|---|---|---|---|---|---|---|---|---|---|---|
| | Day 1 | | | Day 7 | | | Day 30§ | | | Day 150§ | | |
| Tissue | A‡ | B | C | A | B | C | A | B | C | A | B | C |
| Marrow | .006 | .01 | 0.4 | .07 | 0.6 | | 7.0 | 5.0 | 6.5 | 5.0 | 5.0 | 1.0 |
| Spleen | .02 | .008 | 0.1 | 0.1 | | 0.1 | 8.0 | 2.0 | 12.0 | 5.5 | 6.0 | 5.5 |
| Bone | .002 | .0001 | .001 | .0005 | .04 | 0.4 | 9.0 | 10.5 | 4.0 | 5.5 | 4.0 | 2.0 |
| Lung | .001 | <.0001 | <.0001 | .002 | 1.0 | 1.0 | 3.0 | 5.0 | 8.0 | 2.0 | 3.5 | 4.0 |
| Cartilage | | | | | | | | | | 3.0 | 5.0 | 1.5 |
| Brain | | | <.0001 | .005 | .005 | .0005 | .02 | .02 | .02 | 0.1 | 0.6 | 0.2 |

*Percent donor cells were assayed with the two PCR assays shown in FIG. 1. Because the copy number of human mini-gene in the donor cells was about 100:1, the observed values of ratios of the two DNAs were corrected by a factor of 100.
‡Three mice killed on each day were arbitrarily labeled A, B and C.
§Combined values for marrow, spleen, bone and lung for day 30 did not show a statistically significant difference from the combined values for day 150 (means of 6.8% ± 3.02 S.D. and 4.1% ± 6.73 S.D.; n = 12).

We claim:

1. A method of treating a patient who is suffering from a disease, disorder or condition characterized by a bone defect comprising the steps of:
   a) obtaining a bone marrow sample from a donor who is not suffering from a disease, disorder or condition characterized by a bone defect;
   b) isolating adherent cells from said sample; and,
   c) administering by intravenous infusion to said patient an amount of said isolated adherent cells effective to treat said disease, disorder or condition, wherein said patient undergoes bone marrow ablation prior to administration of said isolated adherent cells.

2. The method of claim 1 wherein said adherent cells are administered by intravenous infusion to said patient together with non-adherent cells from a bone marrow sample from a donor who is not suffering from a disease, disorder or condition characterized by a bone defect.

3. The method of claim 1 wherein said disease, disorder or condition is osteogenesis imperfecta.

4. The method of claim 1 wherein said bone defect is due to a collagen gene mutation.

5. The method of claim 1 wherein said donor is syngeneic with said patient.

6. The method of claim 1 wherein said isolated adherent cells are cultured to expand the number of said cells and said expanded culture is administered to said individual.

7. The method of claim 6 wherein said disease, disorder or condition is osteogenesis imperfecta.

8. The method of claim 6 wherein said bone defect is due to a collagen gene mutation.

9. The method of claim 6 wherein said donor is syngeneic with said patient.

* * * * *